(12) United States Patent
Shute et al.

(10) Patent No.: US 11,890,101 B2
(45) Date of Patent: Feb. 6, 2024

(54) CALIBRATION OF IMPLANTABLE DEVICE ORIENTATION

(71) Applicant: Cardiac Pacemakers, Inc., St. Paul, MN (US)

(72) Inventors: Jonathan Bennett Shute, Minnetonka, MN (US); John D. Hatlestad, Maplewood, MN (US); Sunipa Saha, Shoreview, MN (US); David L Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 757 days.

(21) Appl. No.: 16/940,250

(22) Filed: Jul. 27, 2020

(65) Prior Publication Data

US 2021/0030295 A1    Feb. 4, 2021

Related U.S. Application Data

(60) Provisional application No. 62/882,288, filed on Aug. 2, 2019.

(51) Int. Cl.
| | |
|---|---|
| *A61B 5/333* | (2021.01) |
| *A61B 7/04* | (2006.01) |
| *A61B 5/00* | (2006.01) |
| *A61B 5/283* | (2021.01) |
| *A61B 5/363* | (2021.01) |
| *A61N 1/365* | (2006.01) |

(52) U.S. Cl.
CPC ............ *A61B 5/333* (2021.01); *A61B 5/0022* (2013.01); *A61B 5/283* (2021.01); *A61B 5/363* (2021.01); *A61B 5/746* (2013.01); *A61B 7/04* (2013.01); *A61B 2560/0238* (2013.01); *A61B 2562/0219* (2013.01); *A61B 2562/0223* (2013.01); *A61N 1/365* (2013.01)

(58) Field of Classification Search
CPC ......... A61B 5/333; A61B 5/363; A61B 5/283; A61B 5/0022; A61B 5/746; A61B 7/04; A61B 2560/0238; A61B 2562/0219; A61B 2562/0223; A61N 1/365
USPC .................................................. 600/300–301
See application file for complete search history.

(56) References Cited

U.S. PATENT DOCUMENTS

| | | | |
|---|---|---|---|
| 5,593,431 | A | 1/1997 | Sheldon |
| 6,044,297 | A | 3/2000 | Sheldon et al. |
| | | (Continued) | |

*Primary Examiner* — Shirley X Jian
(74) *Attorney, Agent, or Firm* — Schwegman Lundberg & Woessner, P.A.

(57) ABSTRACT

Systems and methods for calibrating an orientation of an implantable device in a patient is described. An exemplary system includes a calibration circuit that can receive acceleration information sensed from an implantable medical device (IMD) implanted in a patient, and receive reference acceleration information sensed from a reference device associated with the patient. The acceleration information and the reference acceleration information are acquired when the patient assumes a first posture or in a first position. The calibration circuit determines a spatial relationship between an orientation of the IMD and a reference orientation of the reference device using the received acceleration information and the received reference acceleration information, and calibrate subsequent acceleration information sensed from the IMD using the determined spatial relationship to correct for the orientation of the IMD.

20 Claims, 9 Drawing Sheets

(56) References Cited

U.S. PATENT DOCUMENTS

| | | |
|---|---|---|
| 8,366,641 B2 | 2/2013 | Wang et al. |
| 8,849,425 B2 * | 9/2014 | Kraetschmer .......... A61B 5/349 |
| | | 600/377 |
| 10,328,267 B2 | 6/2019 | Hatlestad et al. |
| 2010/0010338 A1 | 1/2010 | Van Dam et al. |
| 2010/0223020 A1 * | 9/2010 | Goetz .................. A61B 5/0031 |
| | | 702/104 |
| 2012/0283544 A1 * | 11/2012 | Kraetschmer ........ A61N 1/0504 |
| | | 600/377 |
| 2019/0365290 A1 * | 12/2019 | Lee ....................... A61B 5/1118 |

* cited by examiner

BODY COORDINATES (X, Y, Z)   DEVICE COORDINATES (U, V, W)

IMD COORDINATES                REFERENCE COORDINATES

CALIBRATION OF IMPLANTABLE DEVICE ORIENTATION

CLAIM OF PRIORITY

This application claims the benefit of priority under 35 U.S.C. § 119(e) of U.S. Provisional Patent Application Ser. No. 62/882,288, filed on Aug. 2, 2019, which is herein incorporated by reference in its entirety.

TECHNICAL FIELD

This document relates generally to medical systems, and more particularly, to systems, devices and methods for calibrating an orientation of an implantable device in a patient to improve physiological signal sensing and event detection.

BACKGROUND

An ambulatory medical device (AMD), such as an implantable medical device (IMD), a subcutaneous medical device, a wearable medical device, or other external medical device, may be used to monitor cardiac patient. For example, implantable cardiac devices such as cardiac monitors, pacemakers, defibrillator, or cardiac resynchronization therapy (CRT) devices, have been used for monitoring patient cardiac conditions. Some of these devices can provide therapy to the patient.

Some IMDs include sensors to sense physiological signals from a patient. For example, an IMD may include an accelerometer sensor to detect patient posture or physical activity. Changes in posture or physical activity may be indicative of changes in patient underlying health conditions, and are predictive of worsening of an existing condition, such as heart failure. Frequent patient monitoring can help improve prognosis and patient outcome and reduce hospitalization. Information about patient posture or physical activity may be used to guide therapy. For example, a pacemaker may adjust pacing rate or duration based on patient physical activity. Some IMDs may include a heart sound sensor to sense heart sound information, or an impedance sensor to sense impedance, such as thoracic or cardiac impedance. The heart sound information or the impedance may be used to form medical diagnostics or to titrate a therapy.

The physiological signals sensed from an implanted IMD, such as via electrodes or sensors in the IMD, may be sensitive to IMD orientation in the patient body. For example, some IMDs may rotate, flip, or migrate from its original implanted location and orientation to a different location or a different orientation. The sensed physiological signals may change in amplitude, polarity, timing, or other characteristics. Without proper correction or compensation, some of those changes in signal characteristics associated with IMD orientation may cause inaccurate signal detection and interpretation, and may lead to inappropriate detection of a target event or an inappropriate therapy.

OVERVIEW

The present document discusses systems, devices, and methods for calibrating an orientation of an implantable device implanted in a patient to improve physiological signal sensing and event detection. An exemplary system includes a calibration circuit that can receive acceleration information sensed from an implantable medical device (IMD) implanted in a patient, and receive reference acceleration information sensed from a reference device associated with the patient. The acceleration information and the reference acceleration information are both acquired from the patient while the patient is in a first position, or when the patient assumes the first posture. In certain examples, the acceleration and reference acceleration information can be sensed at the same time, or close in time (e.g., within seconds or minutes, etc.), or confirmed by the patient or a user to be sensed while the patient is in the same position (e.g., the first position). The calibration circuit can determine a spatial relationship between an orientation of the IMD and a reference orientation of the reference device using the received acceleration information and the received reference acceleration information, and calibrate subsequent acceleration information sensed from the IMD using the determined spatial relationship to correct for the orientation of the IMD. The calibrated acceleration information may be used to detect a target event, generate a device diagnostic, or to initiate or adjust a therapy.

Example 1 is a system that comprises a calibration circuit configured to: receive acceleration information sensed from an implantable medical device (IMD); receive reference acceleration information sensed from a reference device associated with the patient, the reference device separate from the IMD; determine a spatial relationship between an orientation of the IMD and a reference orientation of the reference device using the received acceleration information and the received reference acceleration information; and determine the orientation of the IMD or calibrate subsequent acceleration information sensed from the IMD using the determined spatial relationship to correct for the orientation of the IMD.

In Example 2, the subject matter of Example 1 optionally includes the received acceleration information and the received reference acceleration information both acquired with respect to a first posture of the patient, and the reference device that can be a non-implantable device adapted to be adjustably positioned on a body of the patient such that the reference orientation is substantially aligned with a body orientation of the patient in the first posture.

In Example 3, the subject matter of any one or more of Examples 1-2 optionally includes the reference device that can be configured to communicate with the IMD via a wireless communication link. The IMD can include an accelerometer configured to sense the acceleration information, and the reference device can include a reference accelerometer configured to sense the reference acceleration information.

In Example 4, the subject matter of any one or more of Examples 1-3 optionally includes the reference device that can be a personal mobile device.

In Example 5, the subject matter of any one or more of Examples 2-4 optionally includes the subsequent acceleration information that can be sensed from the IMD when the patient assumes a different posture than the first posture, or in a different body position than the first body position.

In Example 6, the subject matter of any one or more of Examples 2-5 optionally includes the received acceleration information that can include acceleration measurements from the IMD along one or more axes, and the received reference acceleration information can include reference acceleration measurements from the reference device along one or more axes. The calibration circuit can be configured to: generate an IMD orientation representation using the acceleration measurements; generate a reference orientation representation using the reference acceleration measurements; and determine the spatial relationship including a rotation matrix that transforms the IMD orientation representation to the reference orientation representation.

In Example 7, the subject matter of Example 6 optionally includes the calibration circuit that can be configured to: receive supplemental acceleration information sensed from the IMD and supplemental reference acceleration information sensed from the reference device, the supplemental acceleration information and the supplemental reference acceleration information concurrently acquired when the patient assumes a second posture different from the first posture; and determine the spatial relationship further using the supplemental acceleration information and the received supplemental reference acceleration information.

In Example 8, the subject matter of Example 7 optionally includes the supplemental acceleration information that can include acceleration measurements from the IMD along one or more axes, and the supplemental reference acceleration information can include reference acceleration measurements from the reference device along one or more axes. The calibration circuit can be configured to: generate an augmented IMD orientation representation using the acceleration measurements and the supplemental acceleration measurements; generate an augmented reference orientation representation using the reference acceleration measurements and the supplemental reference acceleration measurements; and determine the rotation matrix that transforms the augmented IMD orientation representation to the augmented reference orientation representation.

In Example 9, the subject matter of any one or more of Examples 7-8 optionally includes the first posture that can be orthogonal to the second posture.

In Example 10, the subject matter of any one or more of Examples 7-8 optionally includes the first posture being a standing position and the second posture being a lying down position.

In Example 11, the subject matter of any one or more of Examples 7-10 optionally includes the calibration circuit that can be configured to receive the first acceleration information and the first reference acceleration information during an implantation of the IMD.

In Example 12, the subject matter of any one or more of Examples 6-11 optionally includes the calibration circuit that can be configured to: receive magnetic field information sensed from the IMD and receive reference magnetic field information sensed from the reference device, the magnetic field information and the reference magnetic field information both acquired when the patient assumes the first posture or in the first body position, generate an augmented IMD orientation representation using the acceleration measurements and the received magnetic field information; generate an augmented reference orientation representation using the reference acceleration measurements and the received reference magnetic field information; and determine the rotation matrix that transforms the augmented IMD orientation representation to the augmented reference orientation representation.

In Example 13, the subject matter of Example 12 optionally includes the IMD that can include a magnetometer configured to measure a magnetic field, and the reference device can include a reference magnetometer configured to measure a reference magnetic field, when the patient assumes the first posture or in the first body position.

In Example 14, the subject matter of any one or more of Examples 1-13 optionally includes a posture detector configured to detect a posture or a change of posture, and wherein the calibration circuit is configured to calibrate the subsequent IMD acceleration information in response to the detected posture or change of posture.

In Example 15, the subject matter of any one or more of Examples 1-14 optionally includes a detector circuit configured to detect a target physiological event or a status of the IMD using the calibrated subsequent acceleration information. Additionally or alternatively, the subject matter of any one or more of Examples 1-14 optionally includes a user interface configured to generate an alert of the determined IMD orientation.

Example 16 is a method comprising steps of receiving acceleration information from an implantable medical device (IMD); receiving reference acceleration information from a reference device associated with the patient, the reference device separated from the IMD; determining a spatial relationship between an orientation of the IMD and a reference orientation of the reference device using the received acceleration information and the received reference acceleration information; acquiring subsequent acceleration information from the IMD; and calibrating the subsequent acceleration information using the determined spatial relationship to correct for the orientation of the IMD.

In Example 17, the subject matter of Example 16 optionally includes the received acceleration information that can include acceleration measurements from the IMD along one or more axes, and the received reference acceleration information that can include reference acceleration measurements from the reference device along one or more axes. The received acceleration information and the received reference acceleration information can be both acquired with respect to a first posture of the patient. The step of determining the spatial relationship can include: generating an IMD orientation representation using the acceleration measurements; generating a reference orientation representation using the reference acceleration measurements; and determining the spatial relationship including a rotation matrix that transforms the IMD orientation representation to the reference orientation representation.

In Example 18, the subject matter of Example 17 optionally includes the steps of: when the patient assumes a second posture different from the first posture, acquiring supplemental acceleration information from the IMD and acquiring supplemental reference acceleration information from the reference device; and determining the spatial relationship further using the supplemental acceleration information and the received supplemental reference acceleration information.

In Example 19, the subject matter of Example 18 optionally includes the supplemental acceleration information that can include acceleration measurements from the IMD along one or more axes, and the supplemental reference acceleration information that can include reference acceleration measurements from the reference device along one or more axes. The step of determining the spatial relationship can include: generating an augmented IMD orientation representation using the acceleration measurements and the supplemental acceleration measurements; generating an augmented reference orientation representation using the reference acceleration measurements and the supplemental reference acceleration measurements; and determining the rotation matrix that transforms the augmented IMD orientation representation to the augmented reference orientation representation.

In Example 20, the subject matter of Example 19 optionally includes the first posture that can be substantially orthogonal to the second posture.

In Example 21, the subject matter of any one or more of Examples 17-20 optionally includes the steps of: when the patient assumes the first posture or in the first body position, acquiring magnetic field information from the IMD and acquiring reference magnetic field information from the reference device; generating an augmented IMD orientation representation using the acceleration measurements and the received magnetic field information; generating an augmented reference orientation representation using the reference acceleration measurements and the received reference magnetic field information; and determining the rotation matrix that transforms the augmented IMD orientation representation to the augmented reference orientation representation.

In Example 22, the subject matter of any one or more of Examples 16-21 optionally includes detecting a target physiological event or a status of the IMD using the calibrated subsequent acceleration information.

Example 23 is a medical device that comprises a memory circuit and a calibration circuit. The calibration circuit is configured to: receive acceleration information sensed from an implantable medical device (IMD); receive reference acceleration information sensed from a reference device associated with the patient, the reference device separated from the IMD; and determine a spatial relationship between an orientation of the IMD and a reference orientation of the reference device using the received acceleration information and the received reference acceleration information. The memory circuit is configured to store the determined spatial relationship. The calibration circuit is configured to receive subsequent acceleration information from the IMD, and to determine the orientation of the IMD or to calibrate the subsequent acceleration information using the stored determined spatial relationship to correct for the orientation of the IMD.

In Example 24, the subject matter of Example 23 optionally includes the calibration circuit that can be include in the IMD or the reference device.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
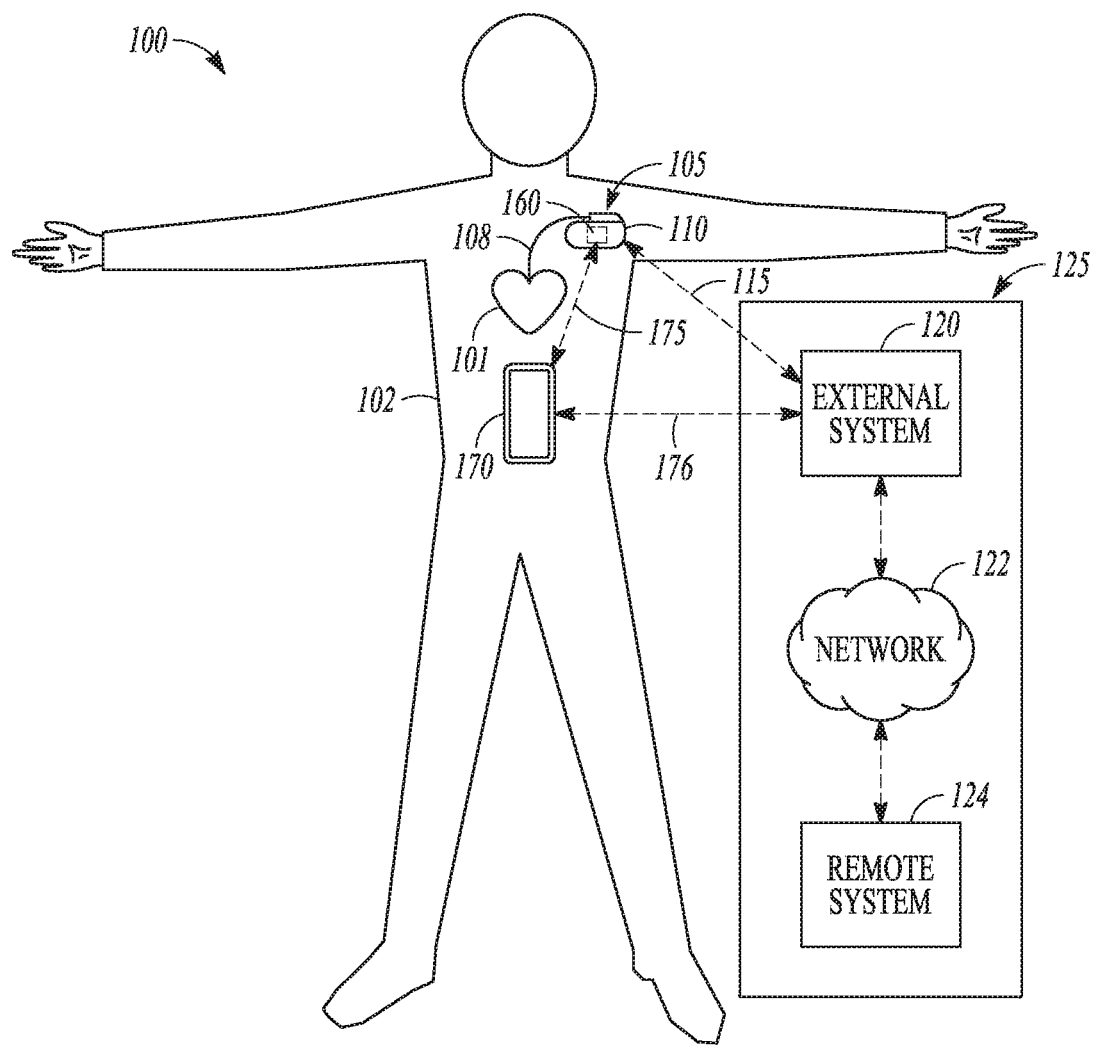
FIG. 1 illustrates generally an example of a patient management system and portions of an environment in which the system may operate.

Ambulatory medical devices, such as IMDs, can sense physiological signals using sensors such as enclosed in or otherwise associated with the medical device. Some of those sensors can be sensitive to IMD orientation in a device pocket at the implant site. Algorithms that utilize the sensed physiological signals for detecting a target physiological event (e.g., cardiac arrhythmia or worsening of heart condition) may be dependent on a fixed IMD orientation, such as an orientation at the time of device implantation. For example, a three-axis accelerometer can measure acceleration in three directions with respect to a presumably fixed IMD orientation in the device pocket of the patient. Patient posture or physical activity level may be detected using the acceleration measurements. In another example, an accelerometer may be configured to detect cardiac vibration or motion, which may be indicative or correlated to heart sounds (HS). One or more HS components, such as first (S1), second (S2), third (S3), or fourth (S4) heart sounds, may be detected from the acceleration signal. Intensity or timing of a HS component may be tracked over time. Algorithms for detecting physical activity and intensity and timing of the HS component may be dependent on a fixed IMD orientation.

However, the IMD orientation may not be fixed in practice, but change over time. For example, some IMDs may migrate away from its initial implant position, rotate, or flip even if the IMD is initially implanted at a body position with proper device orientation. Some IMDs, such as insertable cardiac monitors (ICMs), may be associated with a higher incidence of rotation, flip, or migration, which may be due to their geometries and smaller sizes. In accordance with the changes in MD orientation, one or more signal characteristics (e.g., magnitudes, polarities, timing, temporal pattern, or frequency of spectral content, among others) may also change.

IMD orientation may be calibrated to compensate for the changes in signal characteristics introduced by IMD migration or rotation. Conventionally, such calibration typically takes place in a doctor's office or a device clinic (e.g., for MD checkup). This may have several drawbacks. First, manual testing during an office visit may not ensure a timely detection of changes in IMD orientation such as due to device rotation. The patient may have already experienced consequences such as inappropriate detection, device diagnostics, or device therapy. The delayed detection of IMD rotation may require additional correction procedures, which may cause patient discomfort and increase medical cost. Second, the manual test of changes in IMD orientation can be burdensome to care providers. Such a test may not always be necessary for every patient. For at least these reasons, there is an unmet need for devices and methods of automatic and ambulatory monitoring of IMD orientation and calibration of physiological signals sensed by the IMD to correct for IMD orientation.

This document describes systems, devices, and methods for calibrating an orientation of an IMD in a patient to improve physiological signal sensing and event detection. According to various embodiments, a system or a device can include a calibration circuit to receive acceleration information sensed from an IMD implanted in a patient, and reference acceleration information sensed from a reference device associated with the patient. The acceleration information and the reference acceleration information are both acquired when the patient assumes a first posture or in a first body position. The calibration circuit can determine a spatial relationship between an orientation of the IMD and a reference orientation of the reference device using the received acceleration information and the received reference acceleration information, and calibrate subsequent acceleration information sensed from the IMD using the determined spatial relationship to correct for the orientation of the IMD.

Compared to manual calibration by a clinician at a doctor's office, the calibration techniques discussed herein can be advantageous in that the changes in IMD orientation may be timely detected, burden to the care providers can be reduced, patient outcome can be improved, and overall cost for patient management can be reduced. The IMD orientation calibration discussed in this document also differs from, and is advantageous over conventional approaches. For example, a reference orientation may be established using an external device such as a personal mobile device, which is then used to establish a transformation matrix for transforming an IMD orientation representation to the reference orientation representation. A personal mobile device can be easily adjusted to align with patient natural body axes, and used as a surrogate to patient body orientation with virtually no additional hardware. The proposed use of one or more sensors of different modalities (e.g., accelerometer, magnetometer) in a personal mobile device (e.g., a smart phone) provides a low-cost and easy-to-use solution to an important technological problem of IMD orientation calibration, yet without compromising the calibration performance.

FIG. 1 illustrates generally an example of a patient management system 100 and portions of an environment in which the system 100 may operate. The patient management system 100 may perform a range of activities, including remote patient monitoring and diagnosis of a disease condition. Such activities may be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, insertable cardiac monitors (ICMs), cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiologic signal indicative of cardiac activity, or physiologic responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMD 110 via the lead system 108. The leadless ambulatory sensors may be configured to sense a physiologic signal and wirelessly communicate with the AMD 110.

The AMD 110 may be configured as a monitoring and diagnostic device. An example of such a diagnostic device is an insertable cardiac monitor (ICM) configured to monitor cardiac activity (e.g., heart rate and rhythms) and record them automatically or activated by a user. An ICM can be implanted subcutaneously such as beneath the skin in the upper chest area. The AMD 110 may include a hermetically sealed can that houses one or more of a data receiver circuit, a control circuit, a communication circuit, and a battery, among other components. The data receiver circuit be coupled to one or more sensors or electrodes to sense a physiological signal. The one or more sensors may be incorporated into or otherwise associated with the AMD 110, attached to the housing of the AMD 110, or associated with the AMD 100 or the lead system 108. Examples of the physiologic signals may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, endocardial acceleration or vibration signals, physical activity or exertion level, physiologic response to activity, posture, respiratory rate, tidal volume, respiratory sounds, body weight, or body temperature. The AMD 110 may include circuitry configured to process the received physiological signal, and detect a cardiac status (e.g., cardiac arrhythmia or worsening heart failure) or generate diagnostics, using the processed physiological signal.

As discussed above, the AMD 110 may rotate, flip, or migrate from its original location and orientation at device implantation, and cause changes in one or more characteristics of the received physiological signal. Examples of the signal characteristics that may be affected by the device orientation may include magnitude, polarity, timing, temporal pattern, frequency, or spectral content, among others. One or more of these changes in signal characteristics may cause a detection or diagnostic algorithm implemented in the AMD 110 to inaccurately interpret the received physiological signal, and to make false event detections, diagnostics, or therapy decisions. To compensate for the changes in signal characteristics attributable to device orientation, the AMD 110 may include a device orientation calibration circuit 160 configured to calibrate physiological data sensed by a sensor incorporated into or otherwise associated with AMD 110 (hereinafter referred to as an "AMD sensor"), such as a cardiac acceleration measurements. The calibration is to correct for the orientation of the AMD 110 with respect of patient body orientation, such as due to device rotation, flipping, or migration. The device orientation calibration circuit 160 can receive information from the AMD sensor and information from a reference sensor in a reference device 170. The reference device 170 can be adjustably positioned on patient body such that the reference orientation is substantially aligned with the patient body orientation. The device orientation calibration circuit 160 can determine a spatial relationship between the orientation of the AMD and the reference orientation of the reference device 170 using the information sensed by the AMD sensor and the information sensed by the reference sensor. The device orientation calibration circuit 160 can calibrate subsequent information from the AMD sensor using the determined spatial relationship to correct for the orientation of the AMD. Examples of establishing a spatial relationship and calibrating subsequent acceleration measurements are discussed below, such as with reference to FIG. 2.

In an example, the reference device 170 is a non-implantable device that can be adjustably positioned on the patient body, such as on patient chest. In certain examples, confirmation of the position on the patient body can be confirmed, such as using information received from the patient or a user, prior to or during sensing. Example of the reference device 170 may include a hand-held device, a personal mobile device, a smart phone, or a smart wearable device. In an example, the mobile device can be positioned such that it is in proximity to the AMD 110. In an example, the mobile device can be oriented such that it aligns with patient body axes. The reference device 170 can be communicatively coupled to the AMD 110 via a communication link 175. The communication link 175 is a wireless communication link. The device orientation calibration circuit 160 can receive information sensed by the reference sensor in the reference device 170 via the communication link 175. Additionally or alternatively, the reference device 170 may be communicatively coupled to the external system 125 via a communication link 176, such as a wireless communication link. In some examples, the reference device 170 can be an implantable device separate from the AMD 110. The implantable reference device 170 may have a known or calibrated orientation with respect to the patient body orientation. Examples of the implantable reference device can include a sensor, a pacemaker, an implantable defibrillator, or other implantable devices.

The AMD 110 may be configured as a therapeutic device. In some examples, the AMD 110 may include a therapy unit that may generate and deliver one or more therapies. The therapy may be delivered to the patient 102 via the lead system 108 and the associated electrodes. The therapies may include electrical, magnetic, or other types of therapy. Examples of the anti-arrhythmic therapy may include pacing, cardioversion, defibrillation, neuromodulation, drug therapies, or biological therapies, among other types of therapies. In an example, the therapy unit may be configured to deliver cardiac resynchronization therapy (CRT) or multisite pacing for rectifying dyssynchrony and improving cardiac function in CHF patients. In another example, the therapy unit may be configured to deliver anti-arrhythmic therapy to treat arrhythmias. In yet another example, the therapy unit may be a drug delivery system, such as a drug infusion pump, configured to deliver one or more medications to the patient to treat CHF, arrhythmias, or other physiologic events. The AMD 110 may generate or adjust a therapy based at least on one or more physiological signals received by the AMD 110, or detection of a cardiac event or diagnostic condition generated by the AMD 110. Using the calibrated physiological signal corrected for AMD orientation, such as produced by the device orientation calibration circuit 160, appropriate therapy may be generated and delivered to the patient.

The external system 125 may include a dedicated hardware/software system such as a programmer, a remote server-based patient management system, or alternatively a system defined predominantly by software running on a standard personal computer. The external system 125 may manage the patient 102 through the AMD 110 connected to the external system 125 via a communication link 115. This may include, for example, programming the AMD 110 to perform one or more of acquiring physiologic data, performing at least one self-diagnostic test (such as for a device operational status), reconstructing HS signal, detecting a target physiologic event, or delivering or adjusting a therapy to the patient 102. Additionally, the external system 125 may receive device data from the AMD 110 via the communication link 115. Examples of the device data received by the external system 125 may include real-time or stored physiologic data from the patient 102, diagnostic data such as detection of WHF events, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data may be collected by the AMD 110, among other data acquisition sensors or devices associated with the patient 102. The server may include a memory device to store the patient data in a patient database. The server may include an alert analyzer circuit to evaluate the collected patient data to determine if specific alert condition is satisfied. Satisfaction of the alert condition may trigger a generation of alert notifications. In some examples, the alert conditions alternatively or additionally may be evaluated by the AMD 110. By way of example, alert notifications may include a Web page update, phone or pager call, E-mail, SMS, text or "Instant" message, as well as a message to the patient and a simultaneous direct notification to emergency services and to the clinician. Other alert notifications are possible.

The remote device 124 may additionally include one or more locally configured clients or remote clients securely connected over the network 122 to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

The external system 125, such as the external device 120 or the remote device 124, may output the detected physiologic events, such as an event of WHF, to a system user such as the patient or a clinician, or to a process including, for example, an instance of a computer program executable in a microprocessor. The process may include an automated generation or adjustment of therapy and patient management recommendations. The external system 125 may include respective display units for displaying the physiologic signals, or alerts, alarms, emergency calls, or other forms of warnings to signal the detection of a target physiologic event. The external system 125 may additionally display signal analysis results, such as the reconstructed HS segment, the detected physiologic event, or therapy and patient management recommendations, among other information.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
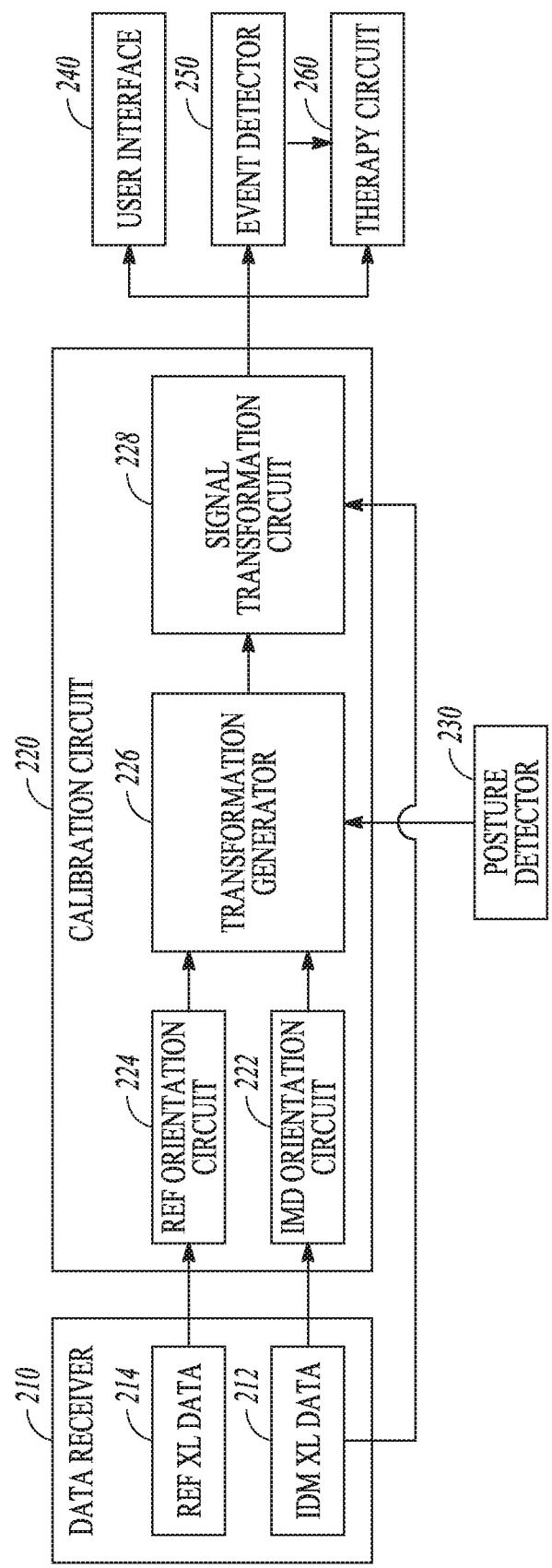
FIG. 2 illustrates generally an example of a device calibration system that can calibrate a physiologic signal received from an IMD to correct for orientation of the IMD.

FIG. 2 illustrates generally an example of a device calibration system 200 configured to calibrate a physiologic signal received from a medical device, such as an implantable medical device (IMD), to correct for orientation of the IMD. The calibration is conducted using an external (i.e., non-implantable) reference device that can provide a reference orientation. The calibrated physiologic signal may be output to a user such as being displayed on a user interface, or to a process such as for detecting a target physiological event such as arrhythmia, worsening heart failure (WHF), or syncope. In some examples, the calibrated physiologic signal may be used for initiating or titrating a therapy. The system 200 may include one or more of a data receiver circuit 210, a calibration circuit 220, a posture detector 230, a user interface 240, an event detector 250, or a therapy circuit 260. At least a portion of the system 200 may be implemented in and executed by the AMD 110, the external system 125 such as one or more of the external device 120 or the remote device 124, or distributed between the AMD 110 and the external system 125.

The data receiver circuit 210 may receive physiologic information from a patient. In an example, the data receiver circuit 210 may include a sense amplifier circuit configured to sense a physiologic signal from a patient via a physiologic sensor, such as an implantable, wearable, or otherwise ambulatory sensor or electrodes associated with the patient. The sensor may be incorporated into or otherwise associated with an implantable medical device (IMD). In some examples, the physiologic signals sensed from a patient may be stored in a storage device, such as an electronic medical record (EMR) system. The data receiver circuit 210 may receive the physiologic signal from the storage device, such as in response to a user command or a triggering event. Examples of the physiologic signals may include surface electrocardiography (ECG) sensed from electrodes placed on the body surface, subcutaneous ECG sensed from electrodes placed under the skin, intracardiac electrogram (EGM) sensed from the one or more electrodes on the lead system 108, heart rate signal, physical activity signal, or posture signal, a thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal, physiologic response to activity, apnea hypopnea index, one or more respiration signals such as a respiratory rate signal or a tidal volume signal, brain natriuretic peptide (BNP), blood panel, sodium and potassium levels, glucose level and other biomarkers and bio-chemical markers, among others. The data receiver circuit 210 may include one or more sub-circuits to digitize, filter, or perform other signal conditioning operations on the received physiologic signal.

In an example, the data receiver circuit 210 may receive, among other physiological information, IMD acceleration (XL) data 212 and reference acceleration (XL) data 214. The IMD XL data 212 may be sensed by a first accelerometer (XL1) integrated into or associated with an IMD. The reference XL data 214 may be sensed by a second accelerometer (XL2) integrated into or associated with a reference device, such as the reference device 170. The IMD XL data 212 and reference XL data 214 may be sensed concurrently under a particular patient condition, such as when the patient assumes a specific posture state ($P_a$), or when the patient is in a first body position.

By way of example and not limitation, the non-implantable reference device can be a mobile device, such as a smart phone. The accelerometers XL1 and XL2 may each be a single-axis accelerometer that measures acceleration in a single direction, or a multi-axis accelerometer, such as a three-axis accelerometer that measures acceleration in three directions. Examples of the accelerometer may include flexible piezoelectric crystal (e.g., quartz) accelerometer or capacitive accelerometer, fabricated using micro electromechanical systems (MEMS) technology. In an example, XL1 and XL2 can be the same type of accelerometer. In another example, XL1 and XL2 can be different types of accelerometers.

The accelerometers XL1 and XL2 may each sense acceleration produced by motion or vibration of the patient body or a part thereof (e.g., a heart, a lung, or a limb). In certain examples, XL1 and XL2 may sense acceleration at the same time, or close in time (e.g., within seconds or minutes, etc.), or confirmed by the patient or a user to be sensed while the patient is in the same position (e.g., the first position). In an example, the sensed acceleration may be indicative of physical activity of a patient. In another example, the sensed acceleration may contain components of vibration or motion produced by heart contraction and relaxation of various structures such as a left ventricle, a right ventricle, a left atrium, or a right atrium. The cardiac vibration and motion may be correlated to heart sounds. In yet another example, the sensed acceleration may contain components correlated to lung sounds, gastric sounds, or guttural sounds. Acceleration signals may also be used to detect or analyze respiration, speech, coughing, swallowing, or snoring, among others.

The calibration circuit 220, which is an embodiment of the device orientation calibration circuit 160, can be configured to generate a spatial relationship between the IMD XL data 212 and reference XL data 214, and calibrate subsequent XL data received from the IMD using the generated spatial relationship. The calibration circuit 220 can be implemented in the IMD, in the reference device 170, in the external system 125, or distributed therebetween. One or more of the IMD XL data 212 or the reference XL data 214 may be transmitted from one device to another, such as between the AMD 110 and the reference device 170 via the communication link 175, between the AMD 110 and the external system 125 via the telemetry link 115, or between the reference device 170 and the external system 125 via the telemetry link 176. The calibration circuit 220 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a processor that may receive and execute a set of instructions of performing the functions, methods, or techniques described herein.

The calibration circuit 220 may include circuit sets comprising one or more other circuits or sub-circuits, such as an IMD orientation circuit 222, a reference orientation circuit 224, a transformation circuit 226, and a signal transformation circuit 228. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Figure 3A:
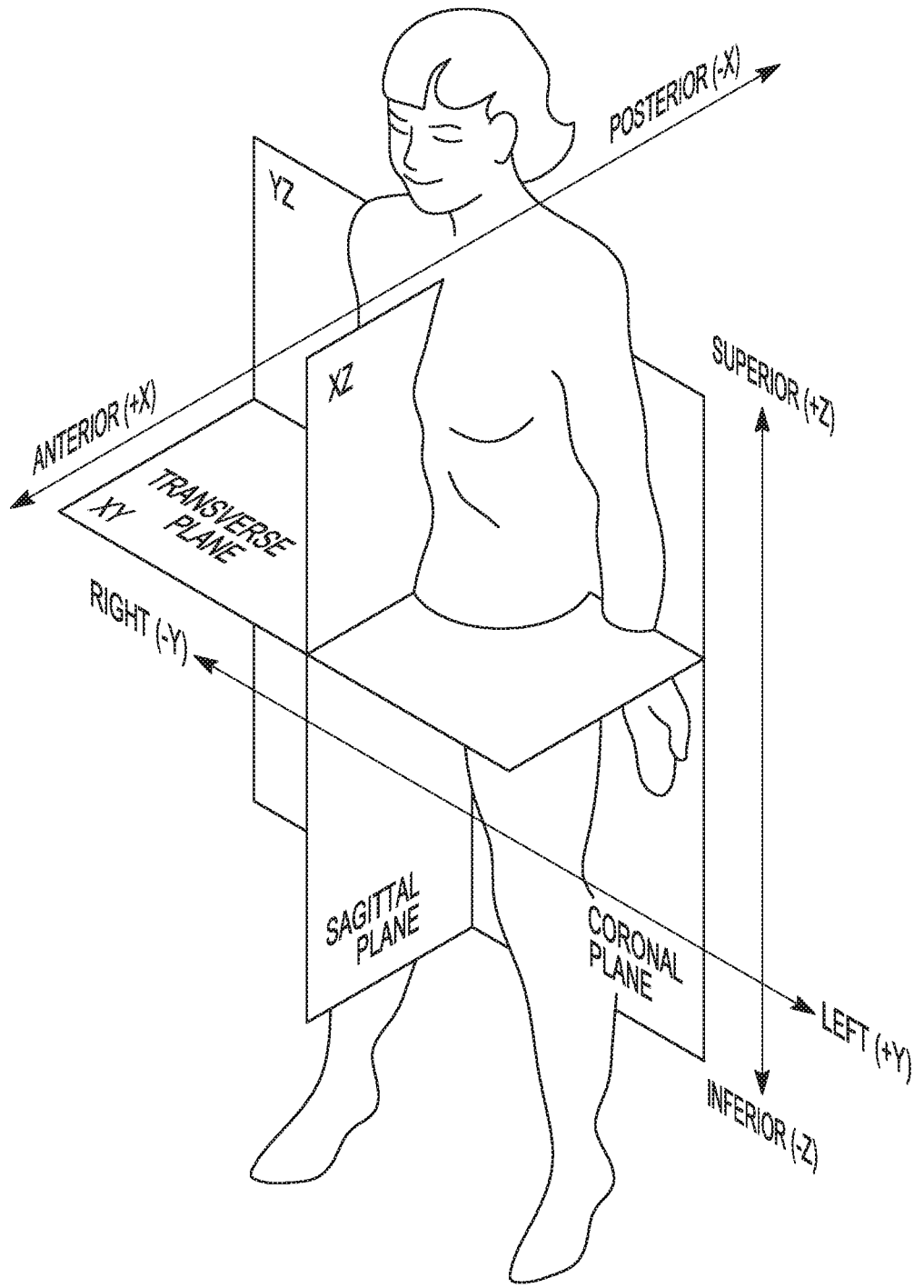
FIGS. 3A-3B illustrate a body coordinate system on a perspective view of a body in an upright position and a device coordinate system.

The IMD orientation circuit 222 can generate a representation of IMD orientation with respect to a gravity or magnetic North when the patient assumes a first posture or in a first body position (e.g., a standing position, or a lying down position). The patient body orientation can be represented by three orthogonal axes, corresponding to the first posture $P_a$. Referring now to FIG. 3A, which illustrates a body coordinate system on a perspective view of a body in an upright position. Three principal anatomical planes are shown. The sagittal plane divides the body into left and right portions. The coronal plane (or frontal plane) divides the body into anterior and posterior portions. The transverse plane divides the body into superior and inferior portions. Corresponding to the three planes are three orthogonal x, y, and z axes that represent a patient body orientation. The frontal axis (y axis) extends along a direction from a medial side to a lateral side of the patient. The longitudinal axis (z axis), also known as superior-inferior axis, extends along a direction from a superior side to an inferior side of the patient. The sagittal axis (x axis), also known as anterior-posterior axis, extends along a direction from an anterior side to a posterior side of the patient.

Figure 3B:
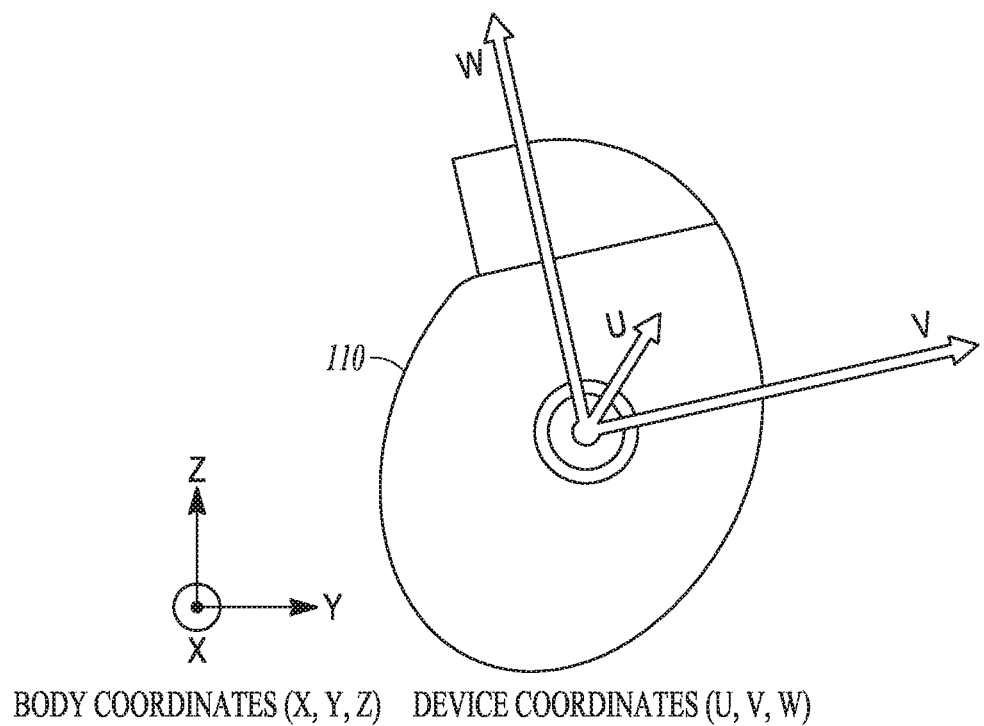

FIG. 3B illustrates a device coordinate system, such as of an AMD 110, represented by u, v, and w axes. A desirable orientation of the AMD 110 can be in the coronal plane such that the device axes substantially match the body axes (e.g., u matches x, v matches y, w matches z). However, a device orientation is not typically in an ideal orientation. The devices axes (u, v, and w) of the AMD 110 may not coincide exactly with the body axes (x, y, and z). For example, in some cases the AMD 110 may possess an implanted orientation that must account for the space available within the patient where the AMD 110 may be situated. Additionally, as discussed above, the AMD 110 may flip, rotate, or migrate, such that its orientation relative to the patient body orientation may change over time. FIG. 3B illustrates by way of example device coordinates are skewed from the body coordinates. According to various embodiments discussed in the present document, acceleration signal sensed by the AMD 110 (such as via XL1) may be compensated for AMD orientation. The compensated acceleration signal may be used to determine patient posture, physical activity, or a physiological condition with improved accuracy. Algorithms such as run by the AMD 110 that use posture sensing can correct for the device orientation.

Referring back to FIG. 2, in an example, the IMD orientation may be represented by a matrix M1 of the measured acceleration data 212 if the IMD acceleration data 212 contains multi-axis acceleration measurements. In the case of a three-axis accelerometer, the matrix M1 has three rows (or three columns) each comprising acceleration measurements along one of the X, Y, and Z axes. In some examples, the IMD orientation circuit 222 may further determine IMD rotational angles relative to the patient body orientation, such as yaw, pitch, and roll angles. The IMD rotational angles can be determined using the measured acceleration data 212 such as according to a method of translating between device coordinates and body coordinates. Commonly assigned U.S. Pat. No. 10,328,267 entitled "METHODS FOR CONSTRUCTING POSTURE CALIBRATION MATRICES," refers to calibrate a posture sensing device for varying orientation, the description of which is incorporated herein by reference in its entirety.

The reference orientation circuit 224 can generate a representation of a reference orientation of the reference device using a similar approach to the IMD orientation representation as discussed above. The reference orientation may be represented by a matrix M2 (in the case of a multi-axis acceleration measurements) of the reference acceleration data 214 sensed by the reference device when the patient is in the same specific posture as that when the IMD acceleration data 212 is acquired. In some examples, the reference orientation circuit 224 may further determine a reference device rotational angles relative to the patient body orientation, using a similar technique as describe above for determining the IMD rotational angles.

In some examples, the IMD orientation circuit 222 may preprocess the IMD XL data 212. In an example, the preprocessing may include filtering the IMD XL data 212 using filters with specific passing/stop band and gain/attenuation effect to extract certain acceleration components of interest, such as those corresponding to body motion/vibration, heart sounds, or lung sounds, etc. In an example, the preprocessing may include an ensemble average of the IMD XL data 212 over a specific time period, such as 5-10 seconds in a non-limiting example. The IMD orientation circuit 222 may generate the representation of an IMD orientation (e.g., matrix M1), or determine an IMD rotational angles, using the preprocessed acceleration data.

The reference acceleration data 214 may be similarly pre-processed. Additionally, in some examples, the reference orientation circuit 224 may validate that the reference device is properly oriented, such as conforming to the patient body orientation within a specified margin when the patient assumes a particular posture. For example, the acquired reference acceleration data is provided to the calibration circuit 220 if the reference acceleration data indicate that the reference device is within 10 degrees of complete vertical when the patient is a standing position, or if the reference acceleration data indicate that the reference device is within 10 degrees of complete horizontal when the patient is in a lying down position. The reference orientation circuit 224 may generate the representation of a reference orientation (e.g., matrix M2) using the preprocessed reference acceleration data.

The transformation generator 226 may determine a spatial relationship between the IMD orientation and the reference orientation. The spatial relationship can be modeled as a linear system with the IMD acceleration representation as input to the system, and the reference acceleration representation as target output of the system. Various techniques, such as system identification techniques, can be used to estimate the spatial relationship. In an example, the spatial relationship is represented by a transformation matrix ($\Phi$), also referred to as a rotation matrix. The transformation matrix $\Phi$ can be determined using matrix M1 (representing IMD orientation) and matrix M2 (representing the reference orientation), such as given in Equation (1). The determined transformation matrix ($\Phi$) can be used to transform a vector of acceleration measurements from the IMD orientation, represented by $V1=[X1, Y1, Z1]^T$, to a vector in the reference orientation, represented by $V2=[X2, Y2, Z2]^T$, as given in Equation (2).

$$\Phi = M2^{-1} \cdot M1 \qquad (1)$$

$$V2 = \Phi \cdot V1 \qquad (2)$$

where $M2^{-1}$ represents an inverse of matrix M2. The determined spatial relationship, such as the transformation matrix $\Phi$, can be stored in a storage device, such as a memory circuit in the IMD 105 or a memory circuit in the reference device 170.

Figure 4:
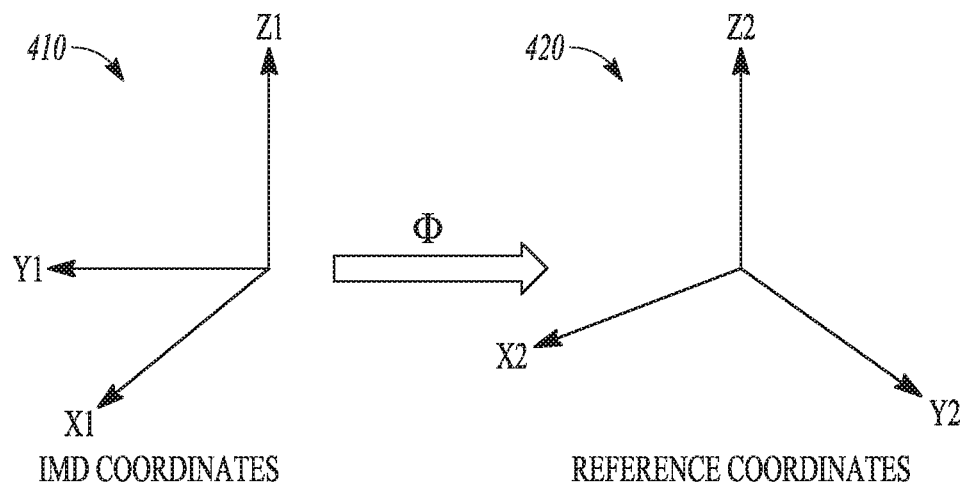
FIG. 4 is diagram illustrating a mapping from an IMD orientation to a reference orientation a reference device through a transformation matrix.

Referring now to FIG. 4, which is a diagram illustrating conceptually a mapping from an IMD orientation 410 of an IMD to a reference orientation 420 of a reference device (e.g., a personal mobile device such as a smart phone) through a transformation matrix $\Phi$. For a particular posture $P_0$, the IMD coordinates 410 are represented by three orthogonal axes: X1, Y1, and Z1. Acceleration data measured from a 3D accelerometer (e.g., XL1) in the IMD can be represented by a three-element vector, V1, with components along the X1, Y1, and Z1 axes which represent the strength of the acceleration in the respective directions. Similarly, the reference coordinates 420 are represented by three orthogonal axes: X2, Y2, and Z2. Acceleration data measured from a 3D accelerometer (e.g., XL2) in the reference device can be represented by a three-element vector, V2, with components along the X2, Y2, and Z2 axes which represent the strength of the acceleration in the respective directions. In the exampled illustrated in FIG. 4, the IMD orientation 410 differs from the reference orientation 420 in that the they have substantially different anterior-posterior direction (X1 vs. X2) and lateral-medial directions (Y1 vs Y2). According to various embodiments discussed in the present document, an optimal transformation matrix $\Phi$ can be found to translate the XL measurements made in IMD orientation 410 to the reference coordinates 420.

Referring back to FIG. 2, the transformation matrix $\Phi$ may be estimated using multiple instances of the vector V1 and multiple instances of the vector V2 respectively measured at different times when the patient assumes the first posture $P_a$. Alternatively, the transformation matrix $\Phi$ may be estimated using multiple instances of the matrix M1 and multiple instances of the matrix M2 respectively measured at different times when the patient assumes the first posture $P_a$. An optimal transformation matrix, denoted by $\Phi^*$, may be determined using an optimization technique such as to minimize a cost function. In an example, the cost function is a mean squared error between the reference acceleration measurements (e.g., M2) and a transformed IMD acceleration representation (e.g., $\Phi \cdot M1$), denoted by $\|M2 - \Phi \cdot M1\|$. In an example, a least-squares method may be used to estimate the transformation matrix. Other cost functions and optimization methods may be used.

To have a robust estimate of the spatial relationship (e.g., the transformation matrix $\Phi$) between the IMD orientation and the reference orientation, particularly in a case of three-axis accelerometer, in some examples, acceleration data acquired respectively when the patient assumes two or more different postures can be used to determine the transformation matrix $\Phi$. For example, the IMD orientation circuit 222 may generate an augmented IMD orientation representation that comprises acceleration data acquired from XL1 when the patient is in a first posture $P_a$ and a second postures $P_b$, respectively. The acceleration data acquired during the second posture $P_b$ is also referred to as supplemental acceleration data. Similarly, the reference orientation circuit 224 may generate an augmented reference orientation representation comprising acceleration data acquired from XL2 when the patient was in the postures $P_a$ and the posture $P_b$. In an example, the first and second postures are not orthogonal to each other. In an example, the first and second postures are substantially orthogonal to each other (e.g., lying down vs. standing upright). In the case of calibrating acceleration measurements using a three-axis accelerometer, the patient body orientations (as well as the orientations of the IMD and the reference device) may differ more significantly for orthogonal postures. The mapping between the IMD orientation and the reference orientation under distinct operating conditions (i.e., postures) may lead to a more robust estimate of an optimal transformation matrix $\Phi$. The resultant optimal transformation matrix $\Phi^*$ may be applied to subsequent IMD acceleration measurements corresponding to a wide range of postures or body positions with a smaller calibration error.

In an example, the augmented IMD orientation representation may be formed using a vector $V1_a$ of acceleration data acquired when the patient assumes a first posture or in a first body position (e.g., standing), and a vector $V1_b$ of acceleration data acquired when the patient assumes a different second posture such as a lying down position (e.g., supine, or prone). Similarly, the augmented reference orientation representation may be formed using a vector $V2_a$ representing reference acceleration data acquired during a standing posture, and a vector $V2_b$ representing reference acceleration data acquired during a lying down position. Alternatively, in some examples, an augmented M1 may be generated from $V1_a$ and $V1_b$ as described in the commonly-assigned U.S. Pat. No. 10,328,267, the description of which is incorporated herein by reference in its entirety. An augmented M2 may similarly be generated from $V2_a$ and $V2_b$ using a similar approach as described in U.S. Pat. No. 10,328,267.

Although two posture states $P_a$ and $P_b$ are discussed herein, they are by way of example and not limitation. Other number of posture states (e.g., three or more), or different combination of posture states, may be used to generate the augmented IMD orientation representation or the augmented reference orientation representation. The transformation generator 226 may determine the spatial relationship, such as the transformation matrix $\Phi$, using the augmented IMD orientation representation (e.g., M1) and the augmented reference orientation representation (e.g., M2).

Patient posture state, such as $P_a$ or $P_b$, may be established in a command mode. Acceleration data acquisition and calibration, hereinafter referred to as a calibration process, can be performed regularly according to a predetermined schedule (e.g., once per month), or triggered by an event such as suspected device migration or rotation in a device pocket. The calibration process can be initiated and monitored at least partially by a human operator, such as the patient or a clinician. In an example, an operator may execute a "calibration protocol" such as via the user interface 240. The calibration protocol includes having a patient remain in a first position or posture, acquiring acceleration data from the IMD and acquiring reference acceleration data from the reference device for a specified time period, then having the patient to switch to and maintain a different second posture, and acquiring acceleration data and the reference acceleration data from respective devices for a specified time period. The acceleration data acquisition may be performed at patient home or in other environment. Alternatively, at least part of the acceleration data acquisition may be performed in a clinic or hospital, such as during implantation of IMD where the patient is in a controlled, known posture (e.g., a lying down position). The IMD acceleration data and the reference acceleration data recorded during device implant may be stored in the device memory for future use. When the patient needs a calibration process, only one posture different from the one during device implant is tested. The acceleration data acquired during this tested posture, along with the stored acceleration data acquired during device implant, are used to form the augmented acceleration data.

Additionally or alternatively, patient posture may be detected automatically using a posture detector 230. The posture detector 230 can be configured to detect a posture state or body position, or a change of posture or a change of body position. In an example, the posture detector includes a tilt switch. In another example, the posture detector 230 includes a camera, which can be located in patient ambient environment, or embedded in the reference device 170 such as a mobile phone. In yet another example, the posture detector is a sleep detector that detects whether or not the patient is lying on the bed. The sleep detection may be based on information such as activity, respiration, heart rate, electrocardiogram, electroencephalogram, among other signals indicative of a sleep or awake state. Alternatively or additionally, the sleep detection may be based on time of a day, under the assumption that patient is likely lying on the bed at certain periods of time during the day such as nighttime. In various examples, different postures may be recognized further using a machine-learning approach that employs patient posture data collected from sensors or a patient device (e.g., the AMD 110). In certain examples, confirmation of the posture or body position can be confirmed, such as using information received from the patient or a user, prior to or during data acquisition. Acceleration data can be stored in a storage device, such as one in the reference device 170 or a device in the external system 125. When a calibration protocol is triggered such as by a user command, a scheduled time (e.g., once per month), or a specific event, the stored acceleration data may be loaded to the calibration circuit 220, which can determine or update the spatial relationship (e.g., a transformation matrix) between the IMD orientation and the reference orientation.

Upon initiation of a scheduled calibration or an event-triggered calibration process, the posture detector 230 may automatically detect two or more different postures. For each detected posture, the reference device and the IMD may concurrently acquire acceleration data for a specified time period. In some examples, data quality and signal duration may be checked against predetermined criterion, such as a minimum duration requirement of acceleration data at a particular posture. Augmented acceleration data may then be generated using the acceleration data corresponding to at least two different posture states.

The signal transformation circuit 228 may calibrate subsequent IMD acceleration data, such as sensed by XL2 of the IMD, to correct for the orientation of the IMD using the determined spatial relationship, such as the optimized transformation matrix $\Phi^*$. The subsequent IMD acceleration data may be acquired during activities of daily living of the patient. The patient may assume a different posture $P_X$ than the postures $P_a$ or $P_b$ for the determination of the transformation matrix $\Phi$. To compensate for the IMD orientation, the subsequent IMD acceleration data, represented by a vector $V1_X$ (which can be generated using a similar method to the generation of $V1_a$ or $V1_b$ as discussed above), may be calibrated using the optimized transformation matrix $\Phi^*$, such as given in Equation (3):

$$cV1_X = \Phi^* \cdot V1_X \quad (3)$$

where $cV1_X$ is the calibrated acceleration vector for the posture $P_X$.

The calibrated acceleration data, such as $cV1_X$, may be provided to a user or a process. The user interface 240 may include an input unit and an output unit. In an example, at least a portion of the user interface 240 may be implemented in the external system 125. In another example, at least a portion of the user interface 240 may be implemented in the reference device 170, such as a user interface of a personal mobile device such as a smart phone. The input unit may receive user input for programming the data receiver circuit 210 and the calibration circuit 220, such as prompting the user and receiving user control for acceleration data acquisition in a calibration protocol, generating transformation matrix, and calibrating subsequent IMD acceleration data. The input unit may include a keyboard, on-screen keyboard, mouse, trackball, touchpad, touch-screen, or other pointing or navigating devices. The output unit may include a display for displaying the calibrated acceleration data, such as $cV1_X$, optionally among with additional measurements or computations. The output unit may also present to a user, such as via a display unit, event detection results such as produced by the event detector 250, or therapy titration or recommended therapy such as produced by the therapy circuit 260, including a change of parameters in the therapy provided by the IMD, the prescription to get a device implanted, the initiation or change in a drug therapy, or other treatment options of a patient. The output unit may include a printer for printing hard copies of information that may be displayed on a display unit. The signals and information may be presented in a table, a chart, a diagram, or any other types of textual, tabular, or graphical presentation formats. The presentation of the output information may include audio or other media format. In an example, the output unit may generate alerts, alarms, emergency calls, or other forms of warnings to signal the system user about the detected medical events. In an example, the calibration circuit may determine the orientation of the IMD using the subsequent acceleration information sensed from the IMD, such as based on a comparison between the received acceleration information and the received reference acceleration information. The output unit of the user interface 240 may present to a user information of the orientation of the IMD, or generate an alert if the IMD orientation indicates the IMD being rotated or flipped from its implant position and orientation.

The event detector 250 may detect a target physiologic event using the calibrated acceleration data, such as $cV1_X$, produced by the calibration circuit 220. In an example, the event detector 250 may generate acceleration signal metrics using the calibrated acceleration data. Using the acceleration signal metrics, the event detector 250 may estimate a sleep incline or other posture measurements, estimate activity, detect characteristics of a heart sound component such as S1, S2, S3, or S4 heart sounds, generate a cardiac function indicator indicating myocardial contractility, cardiac synchrony, and cardiac hemodynamics, or other diagnostics, detect cardiac arrhythmia or discriminate between different arrhythmias (e.g., atrial tachyarrhythmia, supraventricular tachyarrhythmia, or ventricular tachyarrhythmia), detect worsening heart failure, or detect syncope or pre-syncopal conditions. The event detector 250 may additionally or alternatively detect respiratory, renal, neurological, among other medical conditions using the acceleration signal metrics.

In some examples, the event detector 250 may include a device diagnostic circuit configured to detect a device operational state or a change thereof, such as rotation, flip, or migration of the IMD in the pocket. Such device diagnostic may be generated using, for example, a comparison between the IMD orientation representation (M1) and the reference orientation representation (M2), or the optimal transformation matrix $\Phi^*$. In an example, rotational angles in one or more axes may be derived from the transformation matrix $\Phi^*$. The rotational angles indicate a degree of difference between the IMD orientation and the reference orientation. If the rotational angles exceed a threshold, then an alert can be generated to warn the patient or a clinician of possible IMD rotation or flip, or recommended for IMD repositioning, such as via the user interface 240. Additionally or alternatively, the device diagnostic may be used to trigger a recommendation for modifying an IMD operation such as initiating data acquisition at a different time or when patient is in a particular position, modifying an event detection algorithm such as inverting a sensed signal (e.g., heart sound) if the transformation matrix $\Phi^*$ indicates that IMD is completely flipped, etc.

The therapy circuit 260 may be configured to initiate or adjust a therapy delivered to the patient, such as in response to the detected physiologic event. The therapy may be preventive or therapeutic in nature such as to modify, restore, or improve patient neural, cardiac, or respiratory functions. Examples of the therapy may include electrostimulation therapy delivered to the heart, a nerve tissue, other target tissues, a cardioversion therapy, a defibrillation therapy, or drug therapy including delivering drug to the patient. In some examples, the therapy circuit 260 may modify an existing therapy, such as adjust a stimulation parameter or drug dosage. In an example, the calibrated acceleration information produced by the calibration circuit 220 may be used to determine patient physical activity level, and the therapy circuit 260 may adjust cardiac pacing rate or pattern based on patient physical activity level. In another example, the calibrated acceleration information produced by the calibration circuit 220 may be used to determine a change in heart sounds and an indication of worsening heart failure (WHF), and the therapy circuit 260 may adjust electrostimulation therapy or other therapy modalities accordingly.

Figure 5:
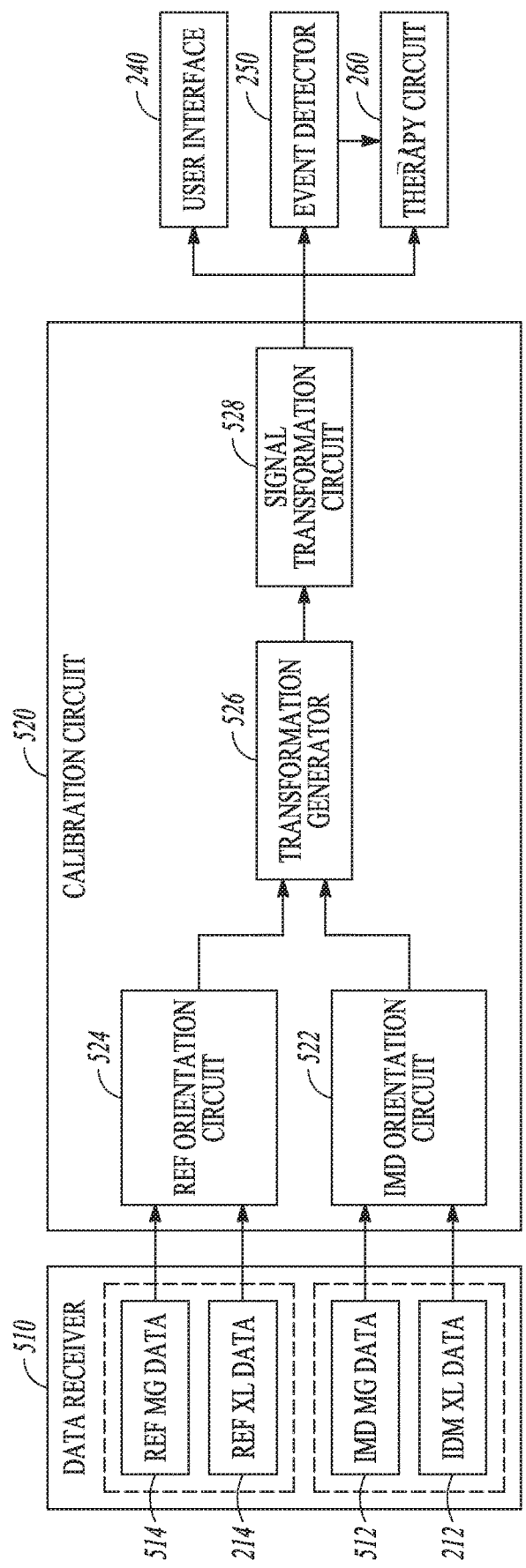
FIG. 5 is a block diagram illustrating an example of a device calibration system to calibrate a physiologic signal received from an IMD to correct for orientation of the medical device using magnetometer sensors.

FIG. 5 is a block diagram illustrating another example of a device calibration system 500 configured to calibrate a physiologic signal received from a medical device such as an IMD, to correct for orientation of the medical device using magnetometer sensors. The system 500, which is a variant of the system 200, may include one or more of a data receiver circuit 510, a calibration circuit 520, and one or more components similarly included in the system 200 including the user interface 240, the event detector 250, or the therapy circuit 260.

The data receiver 510 may receive the IMD XL data 212 such as sensed by the first accelerometer XL1 of an IMD, and the reference XL data 214 such as sensed by the second accelerometer XL2 of a reference device such as the reference device 170 (e.g., a mobile device such as a mobile phone), as discussed above with reference to the data receiver 210. The data receiver 510 may additionally receive MD magnetic field (MG) information 512 and reference magnetic field (MG) information 514. Acquisition of sensor data 212, 214, 512, and 514 may be carried out when the patient in a particular posture state $P_a$.

The IMD MG information 512 may be sensed by a first ambulatory magnetometer (MG1) integrated into or associated with the IMD. The reference MG information 514 may be sensed by a second ambulatory magnetometer (MG2) integrated into or associated with the reference device such as reference device 170. A magnetometer can be a micro-electromechanical (MEMs) device configured to sense where the strongest magnetic force is coming from, generally used to detect magnetic North. The first and second magnetometer, MG1 and MG2, may detect the orientation of respective devices (the IMD and the reference device) relative to the Earth's magnetic field (e.g., magnetic North). Examples of the magnetometer may include a two-axis magnetometer compass that uses two magnetic sensors placed at a right angle to each other with the sensing axes level with respect to gravity, or a three-axis magnetometer compass that uses three magnetic sensors mounted orthogonally and a tilt sensor to determine the gravity vector. In an example, MG1 and MG2 are the same type of magnetometer. In an example, MG1 and MG2 are both three-axis magnetometer compasses.

The calibration circuit 520, which is a variant of the calibration circuit 220, can include an IMD orientation circuit 522, a reference orientation circuit 524, a transformation circuit 526, and a signal transformation circuit 528. The IMD orientation circuit 522 can generate an augmented representation of an IMD orientation using both the IMD acceleration data 212 and the IMD magnetic field data 512. In an example, the IMD acceleration data 212 is a three-axis acceleration data matrix $M1_{XL}$, and the IMD magnetic field data 512 is a three-axis magnetic field data matrix $M1_{MG}$. Assuming the three axes of the XL and the MG are mutually aligned, for computational purposes, the measurements of the MG can be used similarly to the XL measurements as described above to form an augmented IMD orientation representation. Similarly, the reference orientation circuit 524 can generate an augmented representation of a reference orientation using both the reference acceleration data 214 and the reference magnetic field data 514. In an example, the reference acceleration data 214 is a three-axis acceleration data matrix $M2_{XL}$ and the reference magnetic field data 514 is a three-axis magnetic field data matrix $M2_{MG}$.

The transformation generator 526 may determine a spatial relationship, such as the transformation matrix $\Phi$, between the augmented IMD orientation representation and the augmented reference orientation representation. Similar techniques discussed above, such as matrix inverse in Equation (1), a linear regression or a least squares algorithm, may be used to determine an optimal transformation matrix $\Phi^*$. In an example, the transformation matrix $\Phi$ may be estimated using multiple instances of the augmented IMD orientation representation and multiple instances of the augmented reference orientation representation such as measured at different times. The augmented orientation representation that combines acceleration data from an accelerometer and magnet field data from a magnetometer as discussed in this document can be used to form transformation matrix $\Phi$ without requiring two or more different postures.

Similar to the signal transformation circuit 228 of FIG. 2, the signal transformation circuit 528 may calibrate subsequent IMD acceleration data to compensate for the orientation of the IMD using the determined spatial relationship, such as the optimized transformation matrix $\Phi^*$. The subsequent IMD acceleration data may be acquired when the patient is in a different posture state $P_X$ than the posture state $P_a$ corresponding to the data collection for determining the spatial relationship (e.g., the optimal transformation matrix $\Phi^*$). Subsequent IMD acceleration data may be calibrated using the optimized $\Phi^*$, such as according to Equation (3) as discussed above.

In some examples, the reference orientation circuit 524 may further determine an absolute orientation of the reference device in space using the reference XL data 214 and the reference MG data 514. By using the information of magnetic North and gravitational vector from the magnetometer and the accelerometer, the orientation of the device relative to the surface of the earth can be determined. The absolute orientation of the reference device can be used as a surrogate of patient body orientation. The IMD orientation circuit 522 can similarly determine an absolute orientation of the IMD device in space using the IMD XL data 212 and the IMD MG data 512. The transformation generator 526 may determine a spatial relationship between the IMD and the reference device, such as rotational angles between the absolute device orientation and the absolute IMD orientation. The signal transformation circuit 528 may calibrate subsequent IMD acceleration data using the determined spatial relationship (e.g., rotational angles).

Figure 6:
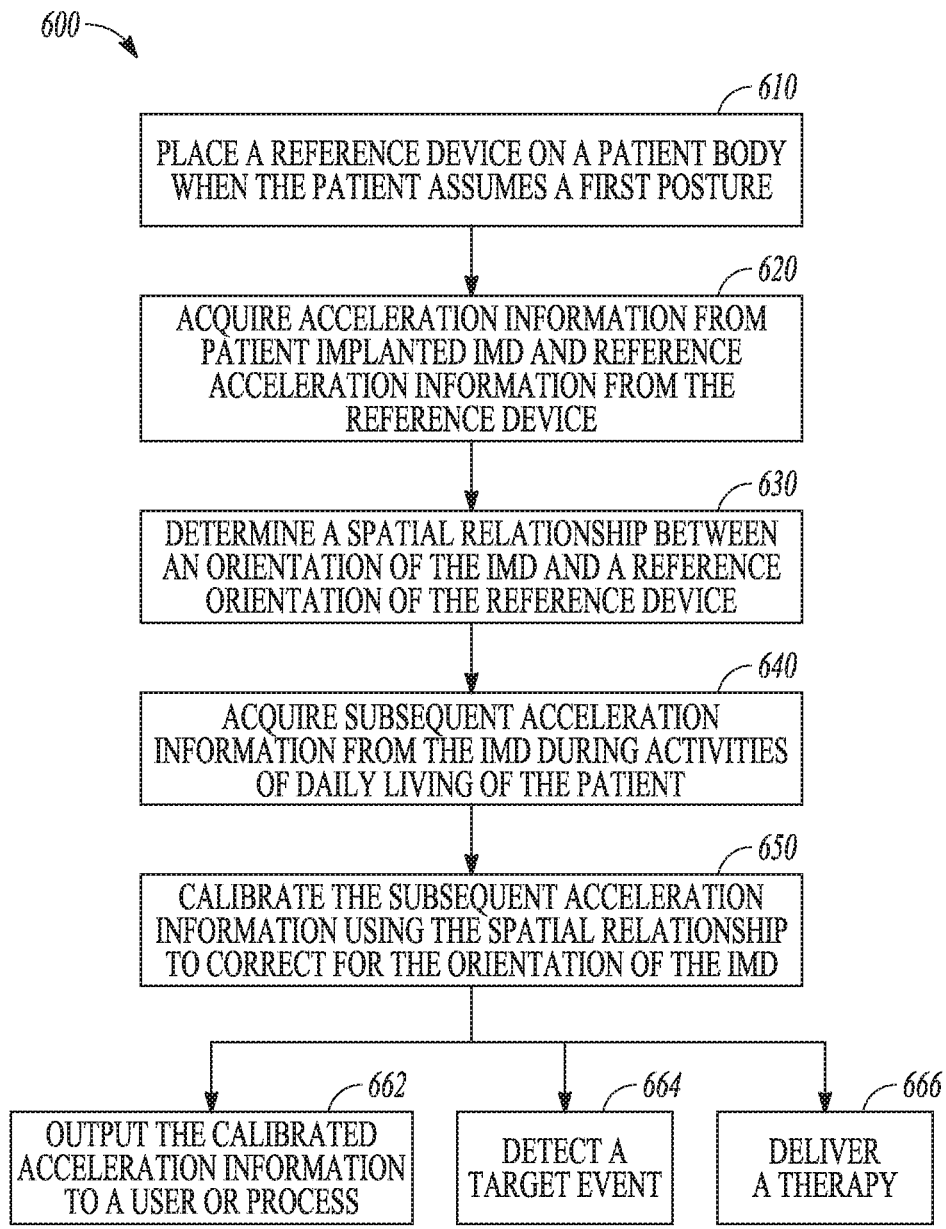
FIG. 6 is a flowchart illustrating an example of a method for calibrating a physiologic signal received from an IMD implanted in a patient to correct for orientation of the IMD.

FIG. 6 is a flowchart illustrating an example of a method 600 for calibrate a physiologic signal received from a medical device, such as an implantable medical device (IMD) implanted in a patient, to correct for orientation of the IMD. The method 600 may be implemented and executed in an ambulatory medical device such as an implantable or wearable medical device, or in a remote patient management system. In an example, the method 600 may be implemented in and executed by the device orientation calibration circuit 160 in the AMD 110, the external system 130, or the device calibration system 200.

The method 600 commences at 610, where a reference device is placed on a patient body when the patient assumes a first posture or in a first body position, such as a standing position or a lying down position (e.g., supine, or prone). An example of the reference device is the reference device 170 as discussed with reference to FIG. 1. The reference device can be a non-implantable device configured to be adjustably positioned on the patient body, such as on the patient chest. In an example, the reference device can be a hand-held device, a personal mobile device, a smart phone, or a smart wearable device. In an example, the reference device may be positioned such that it is in proximity to the IMD implanted in the patient. In an example, the reference device may be oriented such that it is in alignment with patient body axes.

At 620, acceleration information may be acquired from the IMD, such as via a first accelerometer (XL1) integrated into or associated with the MD. Also acquired at 620 includes reference acceleration information from the reference device, such as via a second accelerometer (XL2) integrated into or associated with a reference device. In an example, the XL1 and XL2 may each be a multi-axis accelerometer, such as a three-axis accelerometer configured to sense three-axis acceleration. The acceleration information and the reference acceleration information may be indicative of motion or vibration of the patient body or a part thereof, and are correlative to physical activity, heart sounds, lung sounds, among others. In some examples, the acceleration information and the reference acceleration information may be concurrently acquired when the patient assumes and maintains the first posture.

At 630, a spatial relationship between an orientation of the IMD and a reference orientation of the reference device may be determined using the acquired acceleration information and the reference acceleration information, such as via the calibration circuit 220 of the system 200, or a variant thereof. A representation of IMD orientation with respect to a patient body orientation may be generated using acceleration measurements from the IMD along different axes, such as using the IMD orientation circuit 222. The IMD orientation may be represented by a matrix M1 described above if the accelerometer XL1 is a multi-axis accelerometer. Alternatively, the IMD orientation may be represented by IMD rotational angles relative to the patient body orientation, such as yaw, pitch, and roll angles.

A representation of reference orientation may be generated using the acquired reference acceleration measurements along different axes using a similar approach to construct the IMD orientation representation, such as using the reference orientation circuit 224. The reference orientation may be represented by a matrix M2 of the measured reference acceleration data if the accelerometer XL2 is a multi-axis accelerometer. The reference orientation may alternatively be represented by reference rotational angles relative to the patient body orientation, such as yaw, pitch, and roll angles. In some examples, the acceleration measurements and the reference acceleration measurements may be respectively preprocessed, such as through signal filtering, ensemble averaging, or signal quality check, among others. The IMD orientation representation and the reference orientation representation may be constructed using the respectively preprocessed acceleration data.

A spatial relationship between the IMD orientation and the reference orientation may be determined using the IMD orientation representation and the reference orientation representation, such as using the transformation generator 226. In an example, the spatial relationship may be modeled as a linear system. In an example, the spatial relationship can be represented by a transformation matrix ($\Phi$), also referred to as a rotation matrix. The transformation matrix $\Phi$ can be determined using matrix M1 (representing IMD orientation) and matrix M2 (representing the reference orientation), such as given in Equation (1). In an example, an optimal transformation matrix $\Phi^*$ may be estimated using multiple instances of the vector V1 and multiple instances of the vector V2, or using multiple instances of the matrix M1 and multiple instances of the matrix M2 respectively measured at different times.

At 640, subsequent acceleration information may be acquired from the IMD, such as by using the accelerometer XL1, during activities of daily living of the patient. The patient may assume a different posture than the first posture. The subsequent acceleration information may be represented by an acceleration data vector. Acceleration data measured from a 3D accelerometer (e.g., XL1) in the IMD can be represented by a three-element vector, V1, with components along the X1, Y1, and Z1 axes which represent the strength of the acceleration in the respective directions. Acceleration data measured from a 3D accelerometer (e.g., XL2) in the reference device can be represented by a three-element vector, V2, with components along the X2, Y2, and Z2 axes which represent the strength of the acceleration in the respective directions. At 650, to compensate for the IMD orientation, the subsequent IMD acceleration data may be calibrated using the optimized transformation matrix, such as according to Equation (2).

The calibrated acceleration data, optionally along with other intermediate results such as the optimized transformation matrix, may be provided to a user or a process at 662, such as being displayed on a screen of the user interface 240. Additionally or alternatively, at 664, a target event may be detected based at least on the calibrated acceleration data and/or the optimized transformation matrix $\Phi^*$, such as using the event detector 250. The target event can be a physiological diagnostic or a medical condition, such as an activity level, a sleep incline, a heart sound timing, intensity, or other characteristics, cardiac contractility, hemodynamics, cardiac arrhythmias, syncope or worsening heart failure, among other diagnostics and medical conditions. The target event may alternatively or additionally include device operational state or a change thereof, such as rotation, flip, or migration of the IMD in the pocket. An alert can be generated to warn the patient or a clinician of possible IMD rotation or flip, or recommended for IMD repositioning.

At 666, a therapy may be initiated or adjusted based at least on the calibrated acceleration data and/or the optimized transformation matrix, such as via the therapy circuit 260. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy or treatment plan may be modified to treat the detected arrhythmia, such as modify patient follow-up schedule, or adjust a stimulation parameter or drug dosage.

Figure 7:
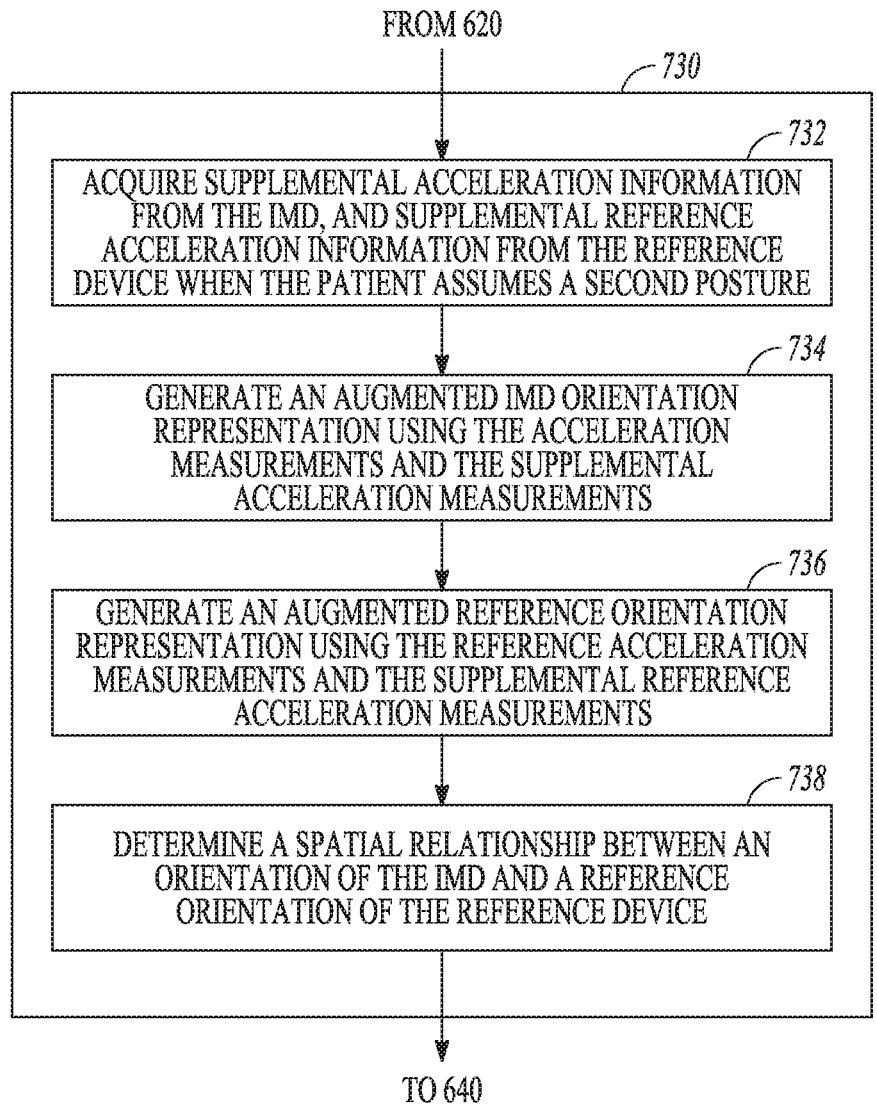
FIG. 7 is a flowchart illustrating an example of a method for determining a spatial relationship between an orientation of an IMD implanted in a patient and a reference orientation of a reference device associated with the patient.

FIG. 7 is a flowchart illustrating an example of a method 730 for determining a spatial relationship, such as a transformation matrix $\Phi$, between the orientation of an IMD implanted in a patient and a reference orientation of a reference device associated with the patient. The method 730 is an embodiment of a portion of the method 600, such as step 630.

The method 730 can be executed after step 620 of method 600. At 732, when the patient assumes a second posture different from the first posture, or when the patient is in a second body position different from the first body position, supplemental acceleration information from the IMD and supplemental reference acceleration information from the reference device may be acquired using respective accelerometers XL1 in the IMD and XL2 in the reference device. In an example, the first and second postures are non-orthogonal to each other. In an example, the first and second postures are substantially orthogonal to each other (e.g., lying down vs. standing upright). For orthogonal postures, the patient body orientations (as well as the orientations of the IMD and the reference device) may differ more significantly. Using acceleration measurements acquired under different postures may lead to a more robust estimate of an optimal transformation matrix $\Phi$. The resultant optimal transformation matrix may be applied to subsequent IMD acceleration measurements, such as according to Equation (3), which may correspond to a wide range of postures or body positions with a small calibration error.

Different postures, such as the first and second postures discussed herein, may be established in a command mode with at least partial user intervention (e.g., by the patient or a system operator). Alternatively, posture or body position, or a change of posture or a change of body position, may be detected automatically, such as using the posture detector 230. In certain examples, confirmation of the posture or body position can be confirmed, such as using information received from the patient or a user, prior to or during data acquisition. The calibration of subsequent IMD acceleration information may be triggered by a detection of a particular posture or a change of posture.

At 734, an augmented IMD orientation representation may be generated, which may include the acceleration measurements and the supplemental acceleration measurements. At 736, an augmented reference orientation representation may similarly be generated, which may include the reference acceleration measurements and the supplemental reference acceleration measurements. The augmented IMD orientation representation and an augmented reference orientation representation may each be constructed in a form of an augmented matrix. At 738, a spatial relationship, such as an optimal transformation matrix, may be determined using the augmented IMD orientation representation and the augmented reference orientation representation, such as using the transformation generator 226. The optimized transformation matrix may then be used to calibrate the subsequent MD acceleration data, according to steps of 640 and 650.

Figure 8:
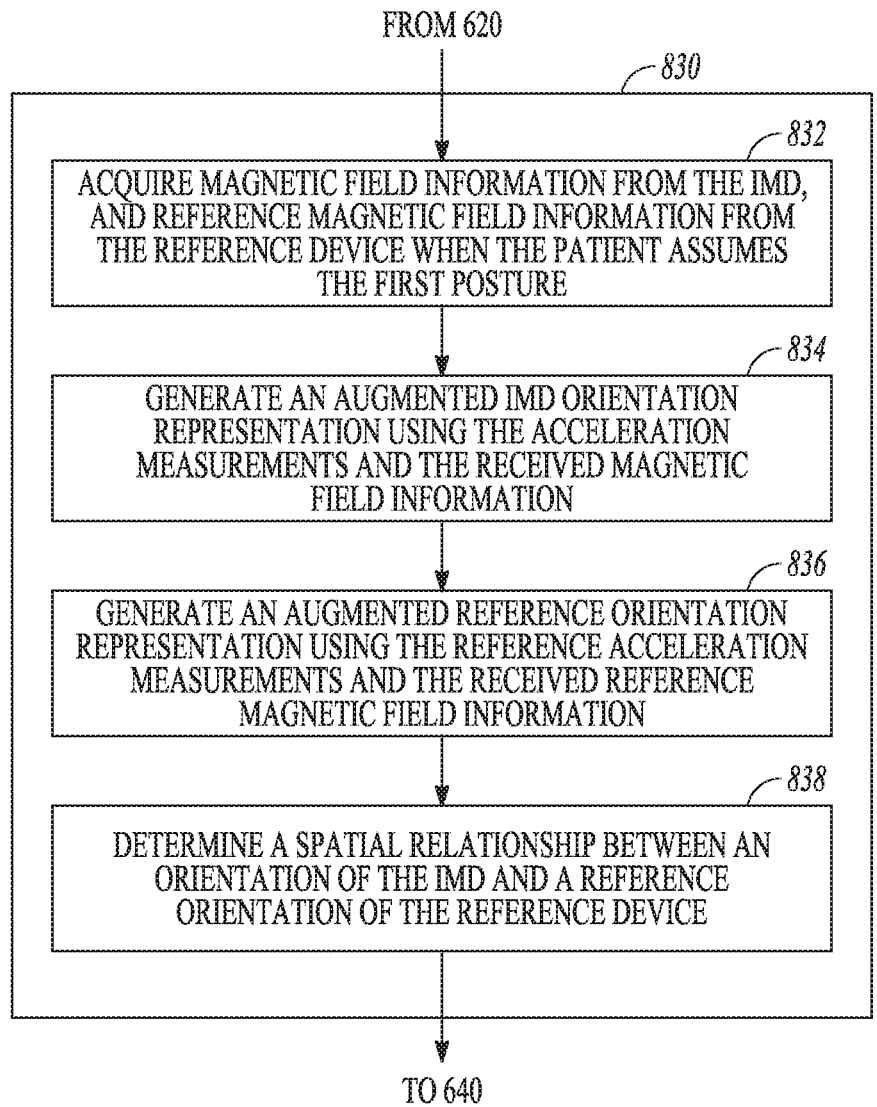
FIG. 8 is a flowchart illustrating another example of a method for determining a spatial relationship between an orientation of an IMD implanted in a patient and a reference orientation of a reference device associated with the patient.

FIG. 8 is a flowchart illustrating another example of a method 830 for determining a spatial relationship, such as a transformation matrix Φ, between the orientation of an IMD implanted in a patient and a reference orientation of a reference device associated with the patient. The method 830 is another embodiment of step 630 of the method 600, and can be implemented in an executed by the device calibration system 500.

At 832, when the patient assumes the first posture or in a first body position, magnetic field information may be acquired from the IMD, such as via a first ambulatory magnetometer (MG1) integrated into or associated with the IMD. Also acquired at 832 includes reference magnetic field information from the reference device, such as via a second ambulatory magnetometer (MG2) integrated into or associated with the reference device. The first and second magnetic field information may be concurrently acquired from the respective magnetometers when the patient is in the first posture. The magnetometers MG1 and MG2 may each detect orientations of respective devices (the IMD and the reference device) relative to the Earth's magnetic field (e.g., magnetic North). Examples of the magnetometer may include a two-axis magnetometer compass or a three-axis magnetometer compass.

At 834, an augmented IMD orientation representation may be generated, which may include the acceleration measurements and the magnetic field information. At 836, an augmented reference orientation representation may similarly be generated, which may include the reference acceleration measurements and the supplemental reference magnetic field information. The augmented IMD orientation representation and an augmented reference orientation representation may each be constructed in a form of an augmented matrix. At 838, a spatial relationship, such as an optimal transformation matrix, may be determined using the augmented IMD orientation representation and the augmented reference orientation representation, such as using the transformation generator 526. The optimized transformation matrix may then be used to calibrate the subsequent IMD acceleration data according to steps of 640 and 650, such as suing the signal transformation circuit 528.

Figure 9:
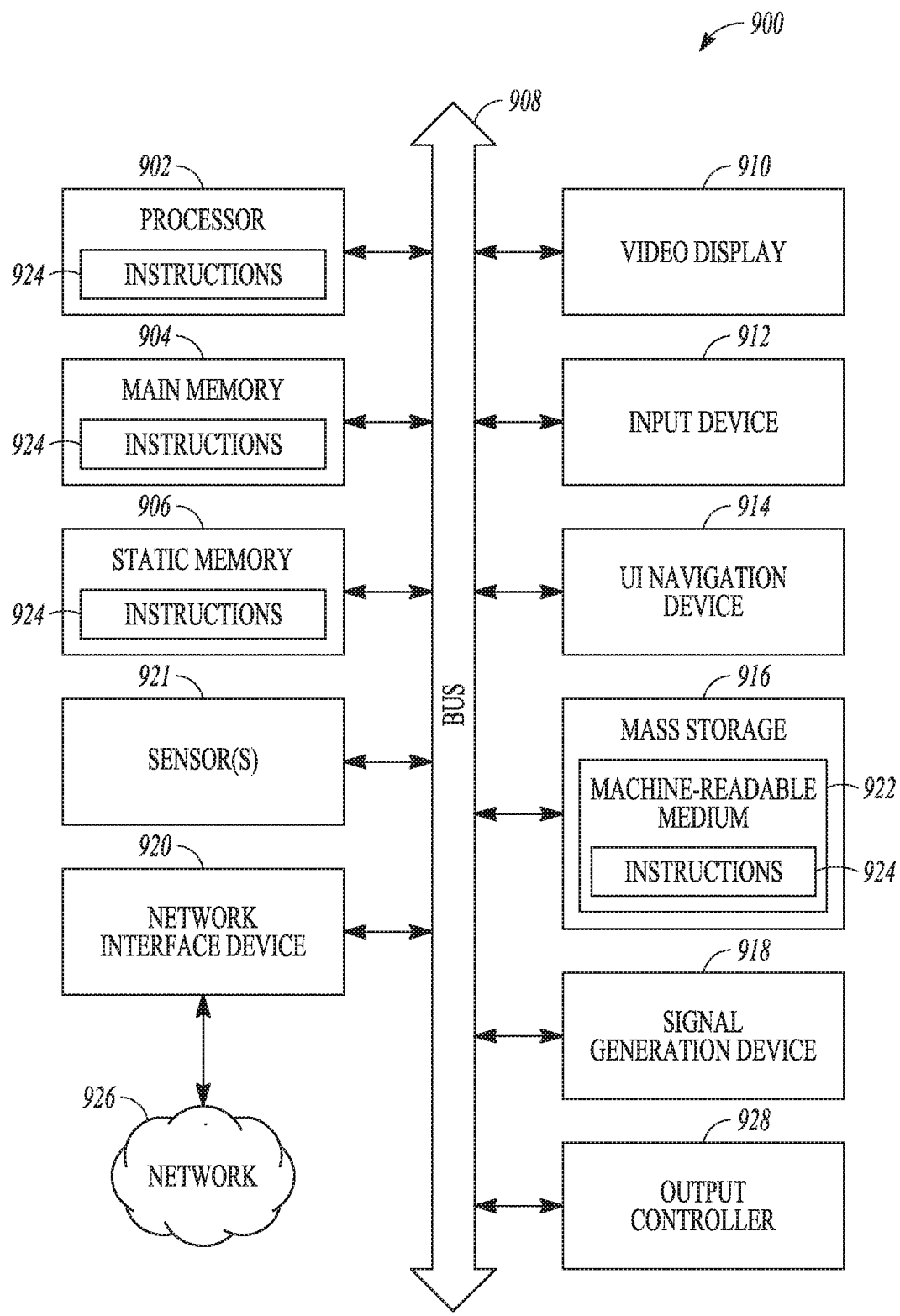
FIG. 9 illustrates generally a block diagram of an example machine upon which any one or more of the techniques (e.g., methodologies) discussed herein may be performed.

FIG. 9 illustrates generally a block diagram of an example machine 900 upon which any one or more of the techniques (e.g., methodologies) discussed herein may perform. Portions of this description may apply to the computing framework of various portions of the AMD, or the external programmer.

In alternative embodiments, the machine 900 may operate as a standalone device or may be connected (e.g., networked) to other machines. In a networked deployment, the machine 900 may operate in the capacity of a server machine, a client machine, or both in server-client network environments. In an example, the machine 900 may act as a peer machine in peer-to-peer (P2P) (or other distributed) network environment. The machine 900 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 900 may include a hardware processor 902 (e.g., a central processing unit (CPU), a graphics processing unit (GPU), a hardware processor core, or any combination thereof), a main memory 904 and a static memory 906, some or all of which may communicate with each other via an interlink (e.g., bus) 908. The machine 900 may further include a display unit 910 (e.g., a raster display, vector display, holographic display, etc.), an alphanumeric input device 912 (e.g., a keyboard), and a user interface (UI) navigation device 914 (e.g., a mouse). In an example, the display unit 910, input device 912 and UI navigation device 914 may be a touch screen display. The machine 900 may additionally include a storage device (e.g., drive unit) 916, a signal generation device 918 (e.g., a speaker), a network interface device 920, and one or more sensors 921, such as a global positioning system (GPS) sensor, compass, accelerometer, or other sensor. The machine 900 may include an output controller 928, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 916 may include a machine readable medium 922 on which is stored one or more sets of data structures or instructions 924 (e.g., software) embodying or utilized by any one or more of the techniques or functions described herein. The instructions 924 may also reside, completely or at least partially, within the main memory 904, within static memory 906, or within the hardware processor 902 during execution thereof by the machine 900. In an example, one or any combination of the hardware processor 902, the main memory 904, the static memory 906, or the storage device 916 may constitute machine readable media.

While the machine-readable medium 922 is illustrated as a single medium, the term "machine readable medium" may include a single medium or multiple media (e.g., a centralized or distributed database, and/or associated caches and servers) configured to store the one or more instructions 924.

The term "machine readable medium" may include any medium that is capable of storing, encoding, or carrying instructions for execution by the machine 900 and that cause the machine 900 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 924 may further be transmitted or received over a communication network 926 using a transmission medium via the network interface device 920 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 920 may include one or more physical jacks (e.g., Ethernet, coaxial, or phone jacks) or one or more antennas to connect to the communication network 926. In an example, the network interface device 920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 900, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system, comprising:
   a calibration circuit configured to:
   receive acceleration information sensed from an implantable medical device (IMD);
   receive reference acceleration information sensed from a reference device associated with a patient, the reference device separate from the IMD;
   determine a spatial relationship between an orientation of the IMD and a reference orientation of the reference device using the received acceleration information and the received reference acceleration information;
   determine the orientation of the IMD or calibrate subsequent acceleration information sensed from the IMD using the determined spatial relationship to correct for the orientation of the IMD; and
   generate a device diagnostic indicative of one or more of a rotation, a flip, or a migration of the IMD based at least in part on the determined orientation of the IMD.

2. The system of claim 1, wherein the received acceleration information and the received reference acceleration information are both acquired with respect to a first posture of the patient, and wherein the reference device is a non-implantable device adapted to be adjustably positioned on a body of the patient such that the reference orientation is substantially aligned with a body orientation of the patient in the first posture.

3. The system of claim 1, wherein the reference device is configured to communicate with the IMD via a wireless communication link, and wherein:
   the IMD includes an accelerometer configured to sense the acceleration information; and
   the reference device includes a reference accelerometer configured to sense the reference acceleration information.

4. The system of claim 1, wherein the reference device is personal mobile device.

5. The system of claim 2, wherein the subsequent acceleration information is sensed from the IMD when the patient assumes a different posture than the first posture.

6. The system of claim 2, wherein the received acceleration information includes acceleration measurements from the IMD along one or more axes, and the received reference acceleration information includes reference acceleration measurements from the reference device along one or more axes, and wherein the calibration circuit is configured to:
- generate an IMD orientation representation using the acceleration measurements;
- generate a reference orientation representation using the reference acceleration measurements; and
- determine the spatial relationship including a rotation matrix that transforms the IMD orientation representation to the reference orientation representation.

7. The system of claim 6, wherein the calibration circuit is configured to:
- receive supplemental acceleration information sensed from the IMD and supplemental reference acceleration information sensed from the reference device, the supplemental acceleration information and the supplemental reference acceleration information acquired when the patient assumes a second posture different from the first posture; and
- determine the spatial relationship further using the supplemental acceleration information and the received supplemental reference acceleration information.

8. The system of claim 7, wherein the supplemental acceleration information includes acceleration measurements from the IMD along one or more axes, and the supplemental reference acceleration information includes reference acceleration measurements from the reference device along one or more axes, and wherein the calibration circuit is configured to:
- generate an augmented IMD orientation representation using the acceleration measurements and the supplemental acceleration measurements;
- generate an augmented reference orientation representation using the reference acceleration measurements and the supplemental reference acceleration measurements; and
- determine the rotation matrix that transforms the augmented IMD orientation representation to the augmented reference orientation representation.

9. The system of claim 7, wherein the first posture is substantially orthogonal to the second posture.

10. The system of claim 6, wherein the calibration circuit is configured to:
- receive magnetic field information sensed from the IMD and receive reference magnetic field information sensed from the reference device, the magnetic field information and the reference magnetic field information both acquired when the patient assumes the first posture;
- generate an augmented IMD orientation representation using the acceleration measurements and the received magnetic field information;
- generate an augmented reference orientation representation using the reference acceleration measurements and the received reference magnetic field information; and
- determine the rotation matrix that transforms the augmented IMD orientation representation to the augmented reference orientation representation.

11. The system of claim 10, wherein the IMD includes a magnetometer configured to measure a magnetic field, and the reference device includes a reference magnetometer configured to measure a reference magnetic field, when the patient assumes the first posture.

12. The system of claim 1, further comprising a detector circuit configured to detect a target physiological event or a status of the IMD using the calibrated subsequent acceleration information.

13. The system of claim 1, further comprising a user interface configured to generate an alert of the determined IMD orientation.

14. A method, comprising:
- receiving acceleration information sensed from an implantable medical device (IMD);
- receiving reference acceleration information sensed from a reference device associated with a patient, the reference device separated from the IMD;
- determining a spatial relationship between an orientation of the IMD and a reference orientation of the reference device using the received acceleration information and the received reference acceleration information;
- acquiring subsequent acceleration information from the IMD;
- determining the orientation of the IMD or calibrating the subsequent acceleration information using the determined spatial relationship to correct for the orientation of the IMD; and
- generating a device diagnostic indicative of one or more of a rotation, a flip, or a migration of the IMD based at least in part on the determined orientation of the IMD.

15. The method of claim 14, wherein the received acceleration information includes acceleration measurements from the IMD along one or more axes, and the received reference acceleration information includes reference acceleration measurements from the reference device along one or more axes, the received acceleration information and the received reference acceleration information both acquired with respect to a first posture of the patient, and wherein determining the spatial relationship includes:
- generating an IMD orientation representation using the acceleration measurements;
- generating a reference orientation representation using the reference acceleration measurements; and
- determining the spatial relationship including a rotation matrix that transforms the IMD orientation representation to the reference orientation representation.

16. The method of claim 15, comprising:
- when the patient assumes a second posture different from the first posture, receiving supplemental acceleration information from the IMD and acquiring supplemental reference acceleration information from the reference device; and
- determining the spatial relationship further using the supplemental acceleration information and the received supplemental reference acceleration information.

17. The method of claim 16, wherein the supplemental acceleration information includes acceleration measurements from the IMD along one or more axes, and the supplemental reference acceleration information includes reference acceleration measurements from the reference device along one or more axes, and wherein determining the spatial relationship includes:
- generating an augmented IMD orientation representation using the acceleration measurements and the supplemental acceleration measurements;
- generating an augmented reference orientation representation using the reference acceleration measurements and the supplemental reference acceleration measurements; and determining the rotation matrix that transforms the augmented IMD orientation representation to the augmented reference orientation representation.

18. The method of claim 15, comprising:

when the patient assumes the first posture, receiving magnetic field information from the IMD and acquiring reference magnetic field information from the reference device;

generating an augmented IMD orientation representation using the acceleration measurements and the received magnetic field information;

generating an augmented reference orientation representation using the reference acceleration measurements and the received reference magnetic field information; and determining the rotation matrix that transforms the augmented IMD orientation representation to the augmented reference orientation representation.

19. A medical device, comprising:

a memory circuit; and a calibration circuit configured to:

receive acceleration information sensed from an implantable medical device (IMD);

receive reference acceleration information sensed from a reference device associated with a patient, the reference device separated from the IMD;

determine a spatial relationship between an orientation of the IMD and a reference orientation of the reference device using the received acceleration information and the received reference acceleration information; and generate a device diagnostic indicative of one or more of a rotation, a flip, or a migration of the IMD based at least in part on the determined orientation of the IMD, wherein the memory circuit is configured to store the determined spatial relationship;

wherein the calibration circuit is configured to receive subsequent acceleration information from the IMD, and to determine the orientation of the IMD or to calibrate the subsequent acceleration information using the stored determined spatial relationship to correct for the orientation of the IMD.

20. The medical device of claim 19, wherein the calibration circuit is included in the IMD or the reference device.

* * * * *